United States Patent
Kubik et al.

(10) Patent No.: US 9,149,675 B2
(45) Date of Patent: Oct. 6, 2015

(54) THERAPY DEVICE FOR TRISMUS PREVENTION AND TREATMENT

(71) Applicant: Helix Medical, LLC, Carpinteria, CA (US)

(72) Inventors: Byron Kubik, Westfield, IN (US); Frank Staples, New Palestine, IN (US); David Eddy, Amherst, MA (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 216 days.

(21) Appl. No.: 13/659,007

(22) Filed: Oct. 24, 2012

(65) Prior Publication Data

US 2014/0113771 A1   Apr. 24, 2014

(51) Int. Cl.
*A63B 21/00* (2006.01)
*A63B 23/03* (2006.01)
*A63B 21/02* (2006.01)

(52) U.S. Cl.
CPC ....... *A63B 21/0004* (2013.01); *A63B 21/00069* (2013.01); *A63B 21/028* (2013.01); *A63B 23/03* (2013.01); *A63B 23/032* (2013.01)

(58) Field of Classification Search
USPC .......................................................... 482/49
See application file for complete search history.

(56) References Cited

U.S. PATENT DOCUMENTS

| | | | |
|---|---|---|---|
| 3,497,217 A * | 2/1970 | Feather | 482/10 |
| 4,909,502 A | 3/1990 | Beeuwkes, III et al. | |
| 5,035,420 A | 7/1991 | Beeuwkes, III et al. | |
| 5,097,820 A | 3/1992 | Shulman et al. | |
| 5,360,385 A * | 11/1994 | Wang | 482/49 |
| 5,361,506 A | 11/1994 | Beeuwkes, III | |
| 5,713,822 A * | 2/1998 | Newman et al. | 482/126 |
| 6,413,231 B1 | 7/2002 | Berman et al. | |
| 2004/0166993 A1 | 8/2004 | Tiberio | |
| 2007/0037665 A1 | 2/2007 | Robbins et al. | |
| 2007/0287598 A1 | 12/2007 | Christensen | |
| 2008/0103026 A1* | 5/2008 | An | 482/49 |
| 2009/0239721 A1* | 9/2009 | Bisson | 482/126 |
| 2010/0011916 A1 | 1/2010 | Christensen, III | |

FOREIGN PATENT DOCUMENTS

| | | |
|---|---|---|
| DE | 69015148 T2 | 6/1995 |
| EP | 0439889 B1 | 12/1994 |
| ES | 2066967 T3 | 3/1995 |

(Continued)

OTHER PUBLICATIONS

DynaSplint; Stretch Beyond Your Expectations catalog; Revision Feb. 2006; (3 pages).

(Continued)

*Primary Examiner* — Jerome w Donnelly
(74) *Attorney, Agent, or Firm* — Daniel J. Sepanik, Esq.; Harness, Dickey & Pierce, P.L.C.

(57) ABSTRACT

A therapy device is provided for trismus prevention and treatment, and includes a first arm hingedly connected to a second arm, and a spring device disposed therebetween to press the first and second arms apart. A pair of bite pads are provided at the ends of each of the first and second arms and are designed to be engaged by a user's teeth or gums in order to bite down on the device to exercise the user's jaw, and more specifically, the muscles of mastication.

17 Claims, 3 Drawing Sheets

(56) References Cited

FOREIGN PATENT DOCUMENTS

| | | | |
|---|---|---|---|
| JP | 4009156 | B2 | 11/2007 |
| WO | 0124757 | A1 | 4/2001 |

OTHER PUBLICATIONS

DynaSplint; Jaw DynaSplint System; http://www.dynasplint.com/divisions/jaw/; Jul. 15, 2010; (pp. 1-4).

* cited by examiner

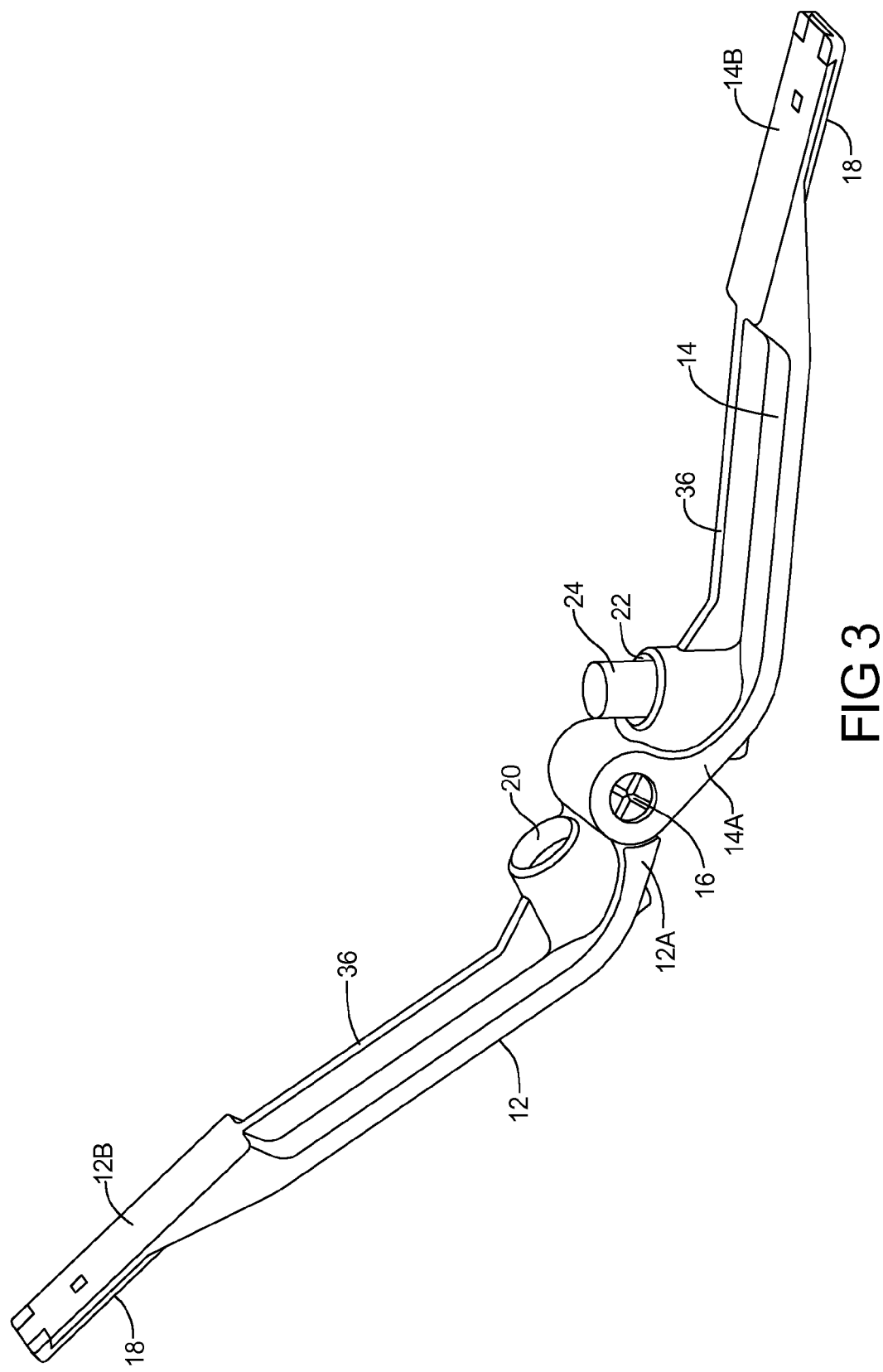

THERAPY DEVICE FOR TRISMUS PREVENTION AND TREATMENT

FIELD

The present disclosure relates to a therapy device for trismus prevention and treatment.

BACKGROUND AND SUMMARY

This section provides background information related to the present disclosure which is not necessarily prior art.

Trismus is a medical complication common in radiation therapy patients that restricts range of motion in the oral cavity. Quality of life can be seriously degraded when patients cannot properly open their mouth.

The device of the present disclosure prevents developing trismus, helps cure it, and acts as a piece of exercise equipment. It uses springs to provide force, opening the mouth to stretch the muscles of mastication. It can also be used to exercise the muscles of mastication by providing resistance when the patient tries to close the device using their muscles.

The therapy device includes a first arm having a first end and a second end, the first arm including a first recess portion disposed between the first end and the second end of the first arm, and a first bite pad disposed at the second end. A second arm includes a first end and a second end, the first end of the second arm being hingedly connected to the first end of the first arm, the second arm including a second recess portion disposed between the first end and the second end of the second arm and opposing the first recess. A second bite pad is disposed at the second end of the second arm. A spring member is received in the first and second recesses and provides resistance when a patient presses against each of the bite pads with their upper and lower teeth. The spring member can be made from an elastomeric material, or other material providing a spring force. The spring members can be press fit in one of the first and second recesses. The first and second arms can include an extra pocket for receiving additional spring members having different spring characteristics. The first and second arms can be generally arch shaped, and the first and second bite pads can include an elastomeric material thereon to prevent the teeth from slipping on the bite pads.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a perspective view of the therapy device shown in a fully open position.

Corresponding reference numerals indicate corresponding parts throughout the several views of the drawings.

DETAILED DESCRIPTION

Figure 1:
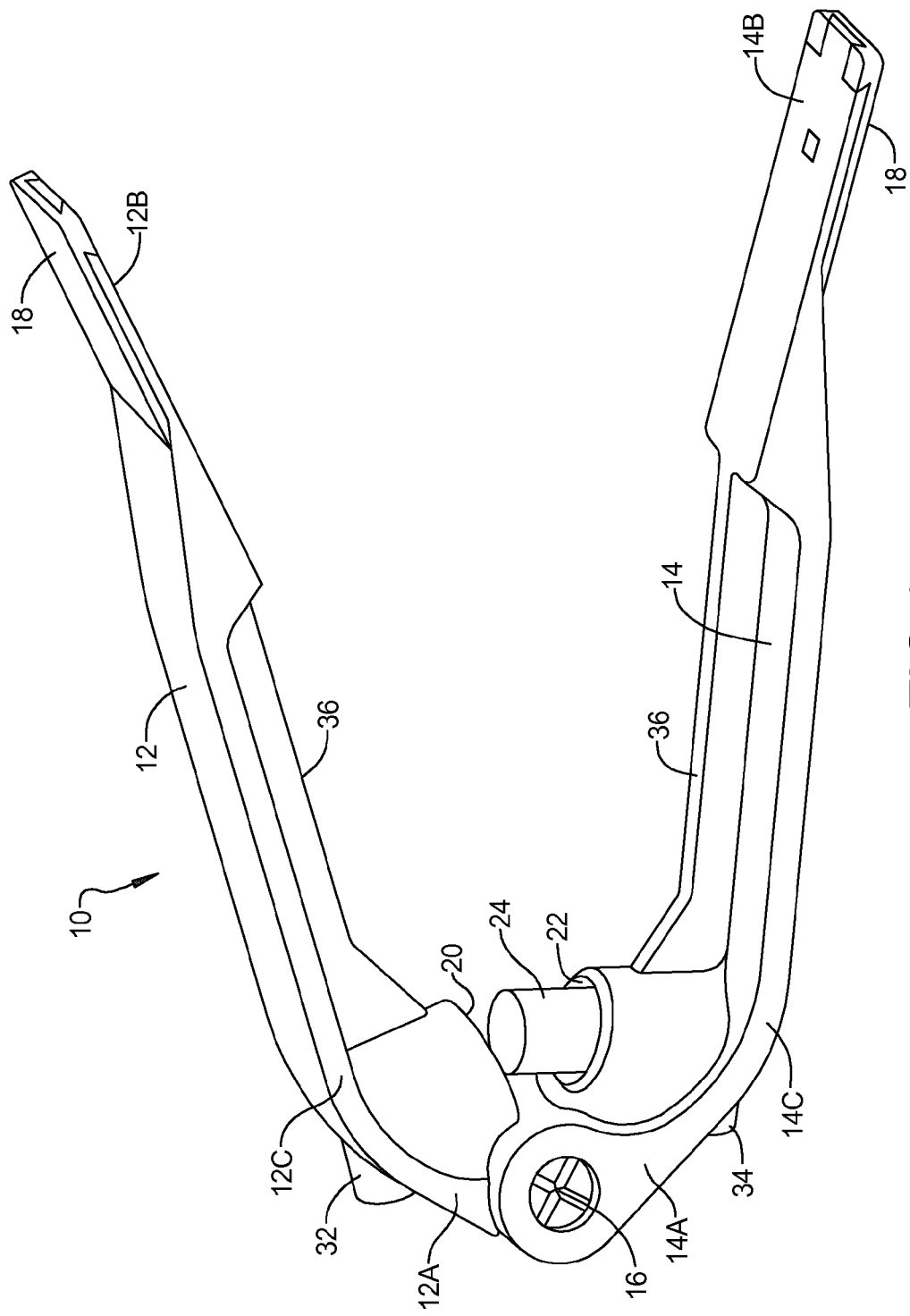
FIG. 1 is a perspective view of the therapy device shown in a partially open position.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

With reference to FIG. 1, a therapy device 10 for trismus prevention and treatment will now be described. The therapy device 10 includes a first arm 12 and a second arm 14, each having a first end 12A, 14A hingedly connected to one another by a pivot pin 16. Each arm 12, 14 includes a bite pad 18 provided on a second end 12B, 14B, respectively. Each arm 12, 14 includes a chamber or recess portion 20 disposed between the first and second ends, and more particularly, adjacent to the first end 12A, 14A of each of the arms 12,14, respectively. Each of the recesses 20, 22 can be generally cylindrically shaped, but could also be any other shape, to receive a cylindrical shaped spring member 24 that can be made of rubber, silicone, or other elastomeric material. The spring member 24 can be generally cylindrical in shape, but could also be any other shape, and can be press fit into one of the recesses 20, 22.

In operation, there are generally two modes. Firstly, to stretch the muscles of mastication to result in an increased range of motion of the jaw, a user manually closes the device and then places their upper and lower teeth, or gums, on the bite pads 18. The user then releases the manual pressure allowing the spring force to open the jaw, thereby stretching the muscles of mastication. With a defined protocol, and over time, there is an increase in the range of motion, as measured by the distance the mouth can be opened. Secondly, the device may be used to exercise the muscles of mastication. In this mode, the user manually closes the device, placing it into their mouth on the bite pads 18. The user then presses the second ends 12B, 14B of the arms 12, 14 toward one another while compressing the spring member 24 within the recesses 20, 22. The spring member provides an appropriate resistance for the user to exercise their muscles of mastication in order to properly treat or prevent trismus.

Figure 2:
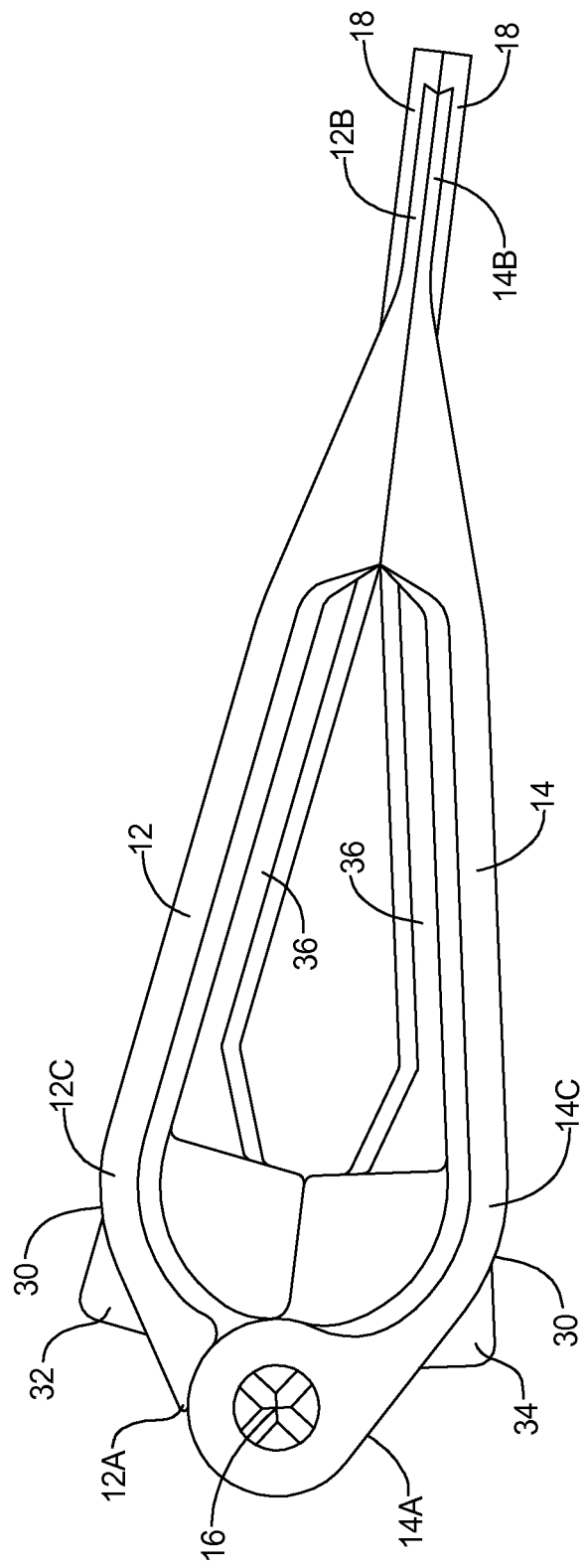
FIG. 2 is a side view of the therapy device shown in a fully closed position.

Each of the first and second arms 12, 14 can be generally arch shaped with a peak 12C, 14C of each arch being disposed closer to the first ends 12A, 14A than the second ends 12B, 14B of each of the arms. This is best illustrated in FIG. 2 wherein the peak 12C, 14C of the arch portion is generally within one quarter of the entire length of the arms from the first end 12A, 14A and is located approximately at the location of the first and second recesses 20, 22. Each of the first and second arms 12, 14 can also be provided with an additional pocket 30 that are provided for receiving additional spring members 32, 34 that can be provided with varying spring characteristics from the first spring member 24. Therefore, the device provides a user with at least three different spring characteristics that can be utilized as the patient's jaw is strengthened. The spring member 24 and additional spring members 32, 34 can be color coded or otherwise marked so as to indicate to the user which spring members have the stiffer spring characteristics.

Each arm 12, 14 can be provided with a reinforcing rib portion 36 that strengthens the arm to prevent bending. The arms 12, 14 and the pivot pin 16 can be made from plastic, metal, or other materials.

The device of the present disclosure can be utilized for the treatment and prevention of trismus and can be utilized to exercise the muscles of mastication. The device uses spring force to stretch open the jaw and exercise the muscles. The device is designed to be small, lightweight, and compact as compared to devices currently on the market. The device is also dishwasher safe for ease of cleaning, and provides a comfortable, soft grip inside the user's mouth. The device is simple to learn and use, and is designed to be used frontally or unilaterally by the patient, and is also usable with or without dentition as the soft bite pads can be used against a patient's gums, if the patient does not have teeth.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A therapy device for trismus prevention and treatment, comprising:
   a first arm having a first end and a second end, said first arm including a first recess portion disposed between said first end and said second end of the first arm and closer to said first end than said second end of the first arm and a first bite pad disposed at said second end;
   a second arm having a first end and a second end, the first end of the second arm being hingedly connected to the first end of the first arm, said second arm including a second recess portion disposed between said first end and said second end of the second arm and closer to said first end than said second end of said second arm and opposing the first recess and a second bite pad disposed at said second end, said first and second bite pads being sized to fit in a user's mouth; and
   a spring member received in said first and second recesses and the second ends of the first and the second arms each having a generally flat opposing surface to be brought flush against one another when the spring member is compressed between the first and second recesses.

2. The therapy device according to claim 1, wherein the spring member is made from an elastomeric material.

3. A therapy device for trismus prevention and treatment, comprising:
   a first arm having a first end and a second end, said first arm including a first recess portion disposed between said first end and said second end of the first arm and closer to said first end than said second end of the first arm and a first bite pad disposed at said second end;
   a second arm having a first end and a second end, the first end of the second arm being hingedly connected to the first end of the first arm, said second arm including a second recess portion disposed between said first end and said second end of the second arm and closer to said first end than said second end of said second arm and opposing the first recess and a second bite pad disposed at said second end, said first and second bite pads being sized to fit in a user's mouth;
   a spring member received in said first and second recesses; and
   wherein at least one of said first and second arms include a pocket for receiving an additional spring member.

4. A therapy device for trismus prevention and treatment, comprising:
   a first arm having a first end and a second end, said first arm including a first recess portion disposed between said first end and said second end of the first arm and closer to said first end than said second end of the first arm and a first bite pad disposed at said second end;
   a second arm having a first end and a second end, the first end of the second arm being hingedly connected to the first end of the first arm, said second arm including a second recess portion disposed between said first end and said second end of the second arm and closer to said first end than said second end of said second arm and opposing the first recess and a second bite pad disposed at said second end, said first and second bite pads being sized to fit in a user's mouth;

a spring member received in said first and second recesses; and wherein each of said first and second arms include a pocket for receiving an additional spring member.

5. A therapy device for trismus prevention and treatment, comprising:

a first arm having a first end and a second end, said first arm including a first recess portion disposed between said first end and said second end of the first arm and closer to said first end than said second end of the first arm and a first bite pad disposed at said second end;

a second arm having a first end and a second end, the first end of the second arm being hingedly connected to the first end of the first arm, said second arm including a second recess portion disposed between said first end and said second end of the second arm and closer to said first end than said second end of said second arm and opposing the first recess and a second bite pad disposed at said second end, said first and second bite pads being sized to fit in a user's mouth;

a spring member received in said first and second recesses; and wherein said spring member is press fit in one of said first and second recesses.

6. The therapy device according to claim 1, wherein said first and second arms are generally arch shaped.

7. The therapy device according to claim 1, wherein said first and second bite pads include an elastomeric material thereon.

8. A therapy device for trismus prevention and treatment, comprising:

a first arch shaped arm having a first end and a second end, said first arm including a first bite pad disposed at said second end;

a second arch shaped arm having a first end and a second end, the first end of the second arm being hingedly connected to the first end of the first arm, said second arm including a second bite pad disposed at said second end, said first and second bite pads being sized to fit in a user's mouth; and a spring member disposed between said first and second arms at a location closer to said first end of said first and second arch shaped arms than said second end of said first and second arch shaped arms and the second ends of the first and the second arms each having a generally flat opposing surface to be brought flush against one another when the spring member is compressed between the first and second arms.

9. The therapy device according to claim 8, wherein the spring member is made from an elastomeric material.

10. A therapy device for trismus prevention and treatment, comprising:

a first arch shaped arm having a first end and a second end, said first arm including a first bite pad disposed at said second end;

a second arch shaped arm having a first end and a second end, the first end of the second arm being hingedly connected to the first end of the first arm, said second arm including a second bite pad disposed at said second end, said first and second bite pads being sized to fit in a user's mouth;

a spring member disposed between said first and second arms at a location closer to said first end of said first and second arch shaped arms than said second end of said first and second arch shaped arms; and wherein at least one of said first and second arms include a pocket for receiving an additional spring member.

11. A therapy device for trismus prevention and treatment, comprising:

a first arch shaped arm having a first end and a second end, said first arm including a first bite pad disposed at said second end;

a second arch shaped arm having a first end and a second end, the first end of the second arm being hingedly connected to the first end of the first arm, said second arm including a second bite pad disposed at said second end, said first and second bite pads being sized to fit in a user's mouth;

a spring member disposed between said first and second arms at a location closer to said first end of said first and second arch shaped arms than said second end of said first and second arch shaped arms; and wherein each of said first and second arms include a pocket for receiving an additional spring member.

12. The therapy device according to claim 8, wherein said first and second bite pads include an elastomeric material thereon.

13. A therapy device for trismus prevention and treatment, comprising:

a first arm having a first end and a second end, said first arm including a first bite pad disposed at said second end;

a second arm having a first end and a second end, the first end of the second arm being hingedly connected to the first end of the first arm, said second arm including a second bite pad disposed at said second end, said first and second bite pads being sized to fit in a user's mouth; and a spring member made from an elastomeric material disposed between said first and second arms, wherein at least one of said first and second arms include a pocket for storing an additional spring member that is not in use between the first and second arms.

14. The therapy device according to claim 13, wherein each of said first and second arms include a pocket for receiving a pair of additional spring members.

15. The therapy device according to claim 14, wherein said pair of additional spring members are press fit in said pocket in said first and second arms.

16. The therapy device according to claim 13, wherein said first and second arms are generally arch shaped.

17. The therapy device according to claim 13, wherein said first and second bite pads include an elastomeric material thereon.

* * * * *